United States Patent [19]

Maniero et al.

[11] Patent Number: 5,213,776
[45] Date of Patent: May 25, 1993

[54] STERILIZER FOR INFANT ACCESSORIES

[75] Inventors: Daniel A. Maniero, Reedsburg; Duane Gerke, North Freedom, both of Wis.

[73] Assignee: Gerber Products Company, Fremont, Mich.

[21] Appl. No.: 406,319

[22] Filed: Sep. 12, 1989

[51] Int. Cl.$^5$ ............................ A61L 2/00; H05B 6/64
[52] U.S. Cl. ................................ 422/303; 422/297; 422/298; 422/300; 422/302; 211/13; 219/10.55 R; 219/10.57; 219/10.67
[58] Field of Search .............. 422/302, 303, 300, 310, 422/297, 298; 211/13, 41, 74; 403/252, 253, 254, 348; 220/360, 361, 367; 219/10.55 R, 10.55 F, 10.57, 10.67

[56] References Cited

U.S. PATENT DOCUMENTS

| | | | |
|---|---|---|---|
| D. 101,396 | 9/1936 | Pipenhagen . | |
| D. 176,310 | 12/1955 | Conlin et al. | D81/10 |
| D. 296,239 | 6/1988 | David | D24/9 |
| 1,951,099 | 3/1934 | Meyerson | 167/3 |
| 2,029,844 | 2/1936 | Tyler | 422/303 |
| 2,141,516 | 12/1938 | Clements | 422/303 |
| 2,467,337 | 4/1949 | Schnell | 21/95 |
| 2,475,407 | 7/1949 | Sell | 422/303 |
| 2,501,193 | 3/1950 | Schulte | 422/303 |
| 3,676,058 | 7/1972 | Gray | 21/54 R |
| 4,142,810 | 3/1979 | Lesaint | 403/252 |
| 4,400,401 | 8/1983 | Beauvais et al. | 426/234 |
| 4,544,529 | 10/1985 | Hoeck | 422/303 |
| 4,646,717 | 3/1987 | Baggioli | 220/367 |
| 4,748,993 | 7/1988 | Llewellyn | 422/297 |
| 4,844,645 | 7/1989 | Rasmussen | 403/254 |
| 4,935,208 | 7/1990 | Köhler | 422/297 |
| 4,952,765 | 8/1990 | Toyosawa | 219/10.55 E |

FOREIGN PATENT DOCUMENTS

| | | | |
|---|---|---|---|
| 351537 | 2/1961 | United Kingdom | 220/367 |
| 2035278 | 6/1980 | United Kingdom | 422/303 |
| 2134788 | 8/1984 | United Kingdom | 422/303 |

OTHER PUBLICATIONS

U.S. design patent application entitled "Sterilizer for Infant Accessories," invented by Daniel A. Maniero and Duane Gerke, filed on even date with the present application and assigned to the same assignee as the present application.

*Primary Examiner*—Robert J. Warden
*Assistant Examiner*—Theresa A. Trembley
*Attorney, Agent, or Firm*—Price, Heneveld, Cooper, DeWitt & Litton

[57] ABSTRACT

A sterilizer assembly for sterilizing infant accessories such as baby bottles, nipples, nipple hoods and collars simultaneously, especially in microwave ovens. Preferably, the assembly is formed from heat resistant, nonmetallic, microwavable materials and includes a base defining a receptacle for receiving water to be heated to form steam. A rack is received on the base over the water and preferably includes a plurality of upstanding supports removably mounted over steam passage apertures in the rack. A dome-like hood encloses the rack, supports, and any items to be sterilized. A vent member on the hood may be rotated to uncover an aperture and release steam from the assembly before removing the hood and after heating to avoid burn injuries. Each support will suspend a baby bottle or, alternately, will suspend a nipple hood, mount a nipple and locate a bottle collar all in position for effective steam contact and water drainage.

40 Claims, 4 Drawing Sheets

STERILIZER FOR INFANT ACCESSORIES

BACKGROUND OF THE INVENTION

This invention relates to sterilizer assemblies for sterilizing various items for human use and, more particularly, to a sterilizer assembly especially adapted for use in a microwave oven to sterilize baby bottles, parts thereof and other infant accessories.

Sterilizers for baby bottles, nipples and other small parts are well-known. Typically, two varieties of sterilizers have been used. A first, such as those shown in Schnell U.S. Pat. No. 2,467,337 and Meyerson U.S. Pat. No. 1,951,099, uses metallic pans containing metallic racks and covered by metallic covers for holding baby bottles and other items. A wire or other metallic support is placed within the pan to hold bottles, nipples and the like over a quantity of water. The pan is then covered and heated on a kitchen range or stove to create steam to cleanse and sterilize the items therewithin.

A second variety of sterilizer, such as those shown in Hoeck U.S. Pat. No. 4,544,529 and David U.S. Pat. No. 296,239, is self-contained and includes its own electrical heating element along with a water container, rack and cover. Steam is created by heating the unit with the self-contained heating element.

With either type sterilizer, and especially those which require an external heat source, most or all of the parts are metallic which prevents their use within microwave ovens. As an alternative, other nonmetallic, microwavable kitchen containers could be used with the baby bottles and parts randomly placed therein. However, the quantity of parts which could be held in such containers was often limited, while the positioning of the baby bottles, nipples and the like within those containers often prevented proper steam contact and sterilization since the bottles were not held in an inverted position and the other parts were placed such that proper drainage could not occur.

Another problem encountered with prior known sterilizers was the possibility of injury when the covers were removed from such units after heating. Typically, when the cover is removed, the trapped steam is released rapidly in a manner which could easily injure the hand or arm of the person opening the assembly. Often, severe burns would result.

In those prior known conventionally heated, metallic sterilizers which contained more complex racks and supports for holding baby bottles and parts, yet another problem became evident, namely, the difficulty in thoroughly cleaning the sterilizer itself. Many of the supporting elements were formed in one piece and included hard to reach corners and spaces which were all but inaccessible for cleaning.

Therefore, the need was apparent for a sterilizer assembly useful in microwave ovens which would provide adequate space and support for baby bottles and their various parts and provide proper cleansing, sterilization and drainage. The present invention was devised in recognition of and as a solution for such need.

SUMMARY OF THE INVENTION

Accordingly, the present invention provides an assembly for sterilizing infant accessories and other items including baby bottles, nipples, nipple hoods and bottle collars all at one time. The assembly is heat resistant and avoids the use of metallic materials thereby enabling use in microwave ovens. The assembly supports various infant accessories in proper position to allow thorough steam contact and drainage. All parts of the assembly may be disassembled for ease in cleaning, while a vent is included to allow release of steam after heating but before the opening of the assembly in order to avoid burns and other injuries.

In one form, the invention is a sterilizer assembly for sterilizing infant accessories and other items including a base having receptacle means for holding a predetermined quantity of water, a rack received on the base for supporting items to be sterilized above the water, the rack including an aperture extending therethrough. An upstanding support is mounted on the rack over the aperture for supporting and/or locating items such as a baby bottle, nipple, nipple hood or bottle collar on the rack. The support includes suspension means for engaging the interior of an item such as a bottle or nipple hood and suspending the item above the aperture with an open end of the item opening downwardly toward the aperture. A dome-like closure or hood is supported on the base for enclosing the rack, support and any items thereon during sterilization.

In other aspects of the invention, the support is removably mounted on the rack to allow ease in removal for cleaning and repair. In a preferred form, the support includes tab members and slots at the end of the support engagable with portions of the rack adjacent the aperture for releasably attaching the support over the aperture.

Preferably, a plurality of supports are mounted on the rack so that several bottles, nipples, nipple hoods or bottle collars can be sterilized simultaneously in the assembly during one operation. In addition to the suspension means, the supports may also include holding means for holding a baby bottle nipple above the aperture, preferably in a position with the opening to the nipple extending laterally of the aperture for proper drainage. Each support is an elongated U-shaped member having generally parallel legs with the tab members for releasably attaching the support to the rack formed at the ends of the legs. Outwardly flared sections in the legs ar provided intermediate the ends of the support for receipt of a nipple.

In yet other aspects of the invention, the hood or closure is telescoped over the base to enclose the rack, support and items to be sterilized, and includes flanges interfitting with the sides of the base to retain the hood or closure thereon. The hood preferably includes a movable vent which may be rotated to cover and uncover an aperture through the hood to allow release of entrapped steam prior to opening of the assembly after heating.

Preferably, all parts of the sterilizer assembly are formed from heat resistant, microwavable material such as general purpose or clarified polypropylene which can withstand temperatures within a range of between about 225° F. and 250° F. without melting or deforming.

As above, the present sterilizer assembly provides numerous advantages over prior known units. Baby bottles, nipples and other infant accessories are properly supported for thorough steam contact and drainage within the assembly. The assembly includes appropriate support for all parts of a baby bottle unit to allow simultaneous sterilization in one operation. The various parts of the assembly are easily disassembled for cleaning and/or repair. In addition, injuries during use are prevented through the provision of a movable vent which may be opened to release entrapped steam prior to general opening of the assembly. Further, the entire unit is formed from microwavable materials enabling use in a microwave oven thereby providing extremely rapid sterilization.

These and other objects, advantages, purposes and features of the invention will become more apparent from a study of the following description taken in conjunction with the drawings.

DESCRIPTION OF THE PREFERRED EMBODIMENTS

Figures 1, 2, 10, 11:
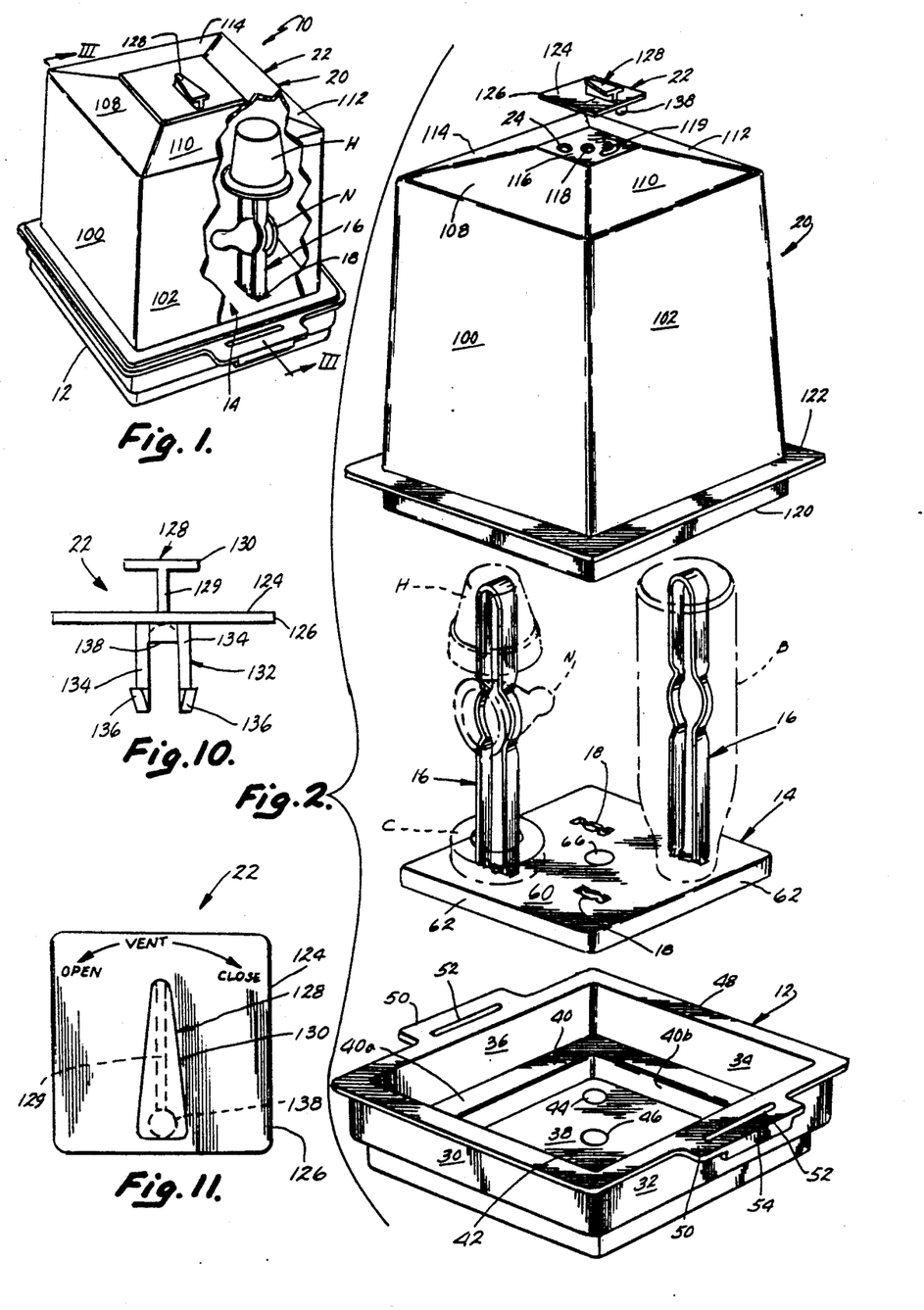
FIG. 1 is a perspective view of the sterilizer assembly of the present invention with portions broken away to reveal support of a nipple and a nipple hood on one of the supports of the assembly.
FIG. 2 is an exploded perspective view of the various parts of the sterilizer assembly shown in FIG. 1 illustrating support of a baby bottle, nipple hood, nipple and bottle collar simultaneously within the assembly.
FIG. 10 is an end elevation of the vent closure/handle.
FIG. 11 is a top plan view of the vent closure/handle of FIG. 10.
Figure 3:
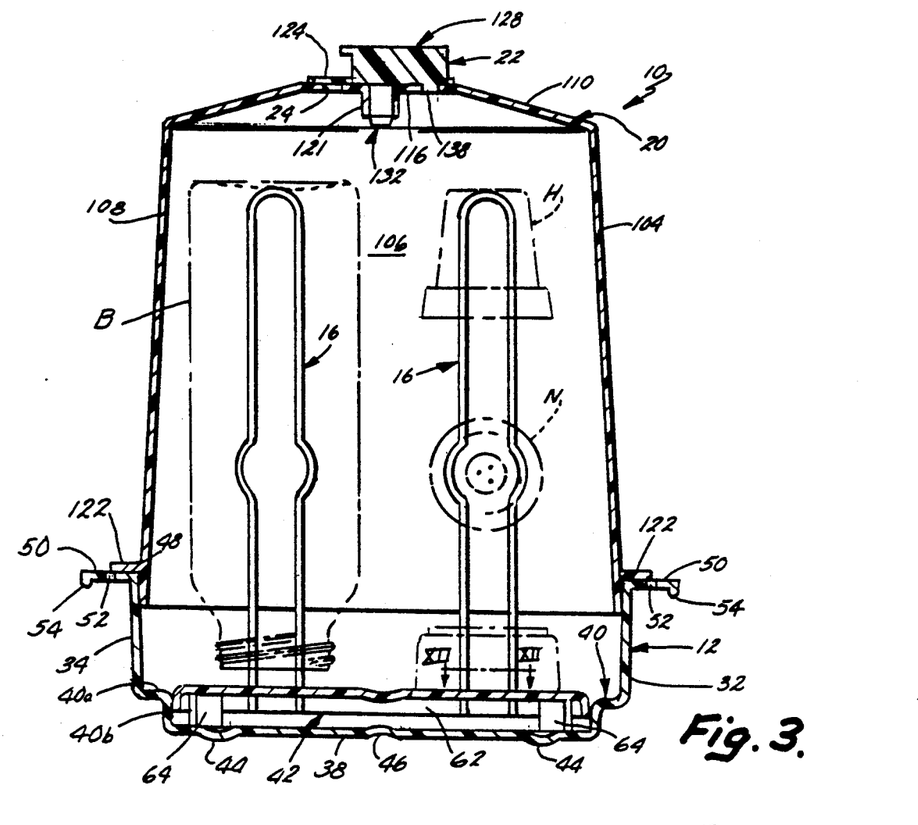
FIG. 3 is a sectional front elevation of the sterilizer assembly taken along plane III—III of FIG. 1.

Referring now to the drawings in greater detail, FIGS. 1-3 illustrate a preferred embodiment 10 of the sterilizer assembly of the present invention. The assembly includes a base 12 receiving a separate rack 14 on its interior bottom surface. A plurality of upstanding supports 16 are removably secured over spaced steam passage apertures 18 extending through rack 14. Each support may receive a baby bottle B suspended thereover or, alternately, one or more of a nipple N, nipple hood H or bottle collar C thereon and within the assembly at any one time. Since, in the preferred embodiment, four supports 16 are included over four separate apertures 18 up to four baby bottles without accompanying parts can be sterilized simultaneously. Alternately, two complete baby bottles including nipples, nipple hoods and collars can be sterilized simultaneously. A hood or dome-like closure 20 is received over rack 14, supports 16 and any bottles, bottle parts or other infant accessories such as pacifiers supported thereon to enclose those parts and provide a chamber for the generation of steam from water contained in the bottom of base 12 during heating. Base 12, rack 14, supports 16 and hood or closure 20 are each formed from heat resistant, nonmetallic, microwavable materials such that the entire assembly may be placed within a microwave oven for rapid heating, steam formation and sterilization. After heating, a rotatable vent member 22 at the top of hood 20 is rotated to open a vent aperture 24 in the hood to release steam from the interior of the assembly. This prevents injury upon removal of the hood when access to the fully sterilized baby bottles and parts is desired.

Figure 4:
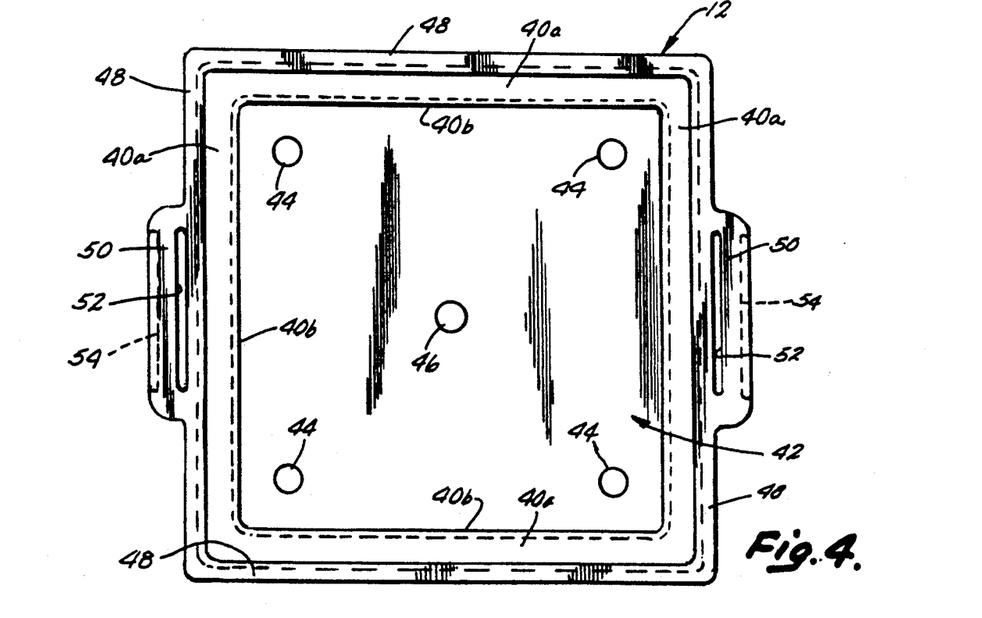
FIG. 4 is a top plan view of the base for the sterilizer assembly.

As will be best seen from FIGS. 2-4, base 12 is molded in one piece and has a square configuration including upstanding sidewalls 30, 32, 34 and 36 which are integrally joined to bottom wall 38 by means of a continuous shoulder 40. Shoulder 40 extends around the interior of sidewalls 30-36 and includes horizontal wall 40a and vertical wall 40b integrally joined with one another, sidewalls 30-36 and bottom wall 38. Vertical walls 40b in conjunction with bottom 38 define the perimeter of a recessed receptacle 42 which is concentric with the square recess formed by the sidewalls 30-36. Receptacle 42 is adapted to receive a predetermined quantity of water which, when the assembly is heated, generates steam for sterilization of the infant accessories or other items contained within the assembly. Receptacle 42 also receives rack 14 as shown in FIG. 3 and described more fully hereinafter.

As shown in FIGS. 2-4, bottom wall 38 includes four spaced spherical depressions 44 adjacent the corners of the bottom wall. Depressions 44 project downwardly an equal distance to support the assembly slightly above a support surface. A central depression 46 projects upwardly and provides a break-off area for the plastic injection sprue runner during molding of base 12. Sidewalls 30-36 include a top flange 48 defining a co-planar uppermost surface of base 12. Flange 48 is continuous and extends around the entire upper perimeter of the base. Extending laterally outwardly from flange 48 on two of the opposing sidewalls, such as sidewalls 32, 36, are handles 50 molded integrally with flange 48 and projecting in co-planar fashion therefrom such that they are flush with flange 48. Handles 50 each include a slot 52 passing entirely through the handle to reduce conduction of heat from base 12 to the handle and allow better cooling of the handle. Also, each handle includes a downwardly projecting lip 54 providing a finger grip when the assembly is lifted by the handles.

As shown in FIGS. 2, 3, 6 and 7, rack 14 is molded in one piece and includes a substantially planar shelf or platform 60 including integrally molded sidewalls 62 providing rigidity for the shelf. Four downwardly projecting, L-shaped feet 64 are molded on the underside of the rack, one being provided adjacent each corner of the rack. Feet 64 are spaced slightly inwardly from the corners of rack 14 such that they rest on bottom wall 38 between the corners formed by walls 40b and depressions 44. As with depression 46 on base 12, a slight depression 66 is formed at the center of shelf 6 to aid in molding of the rack.

Figure 6:
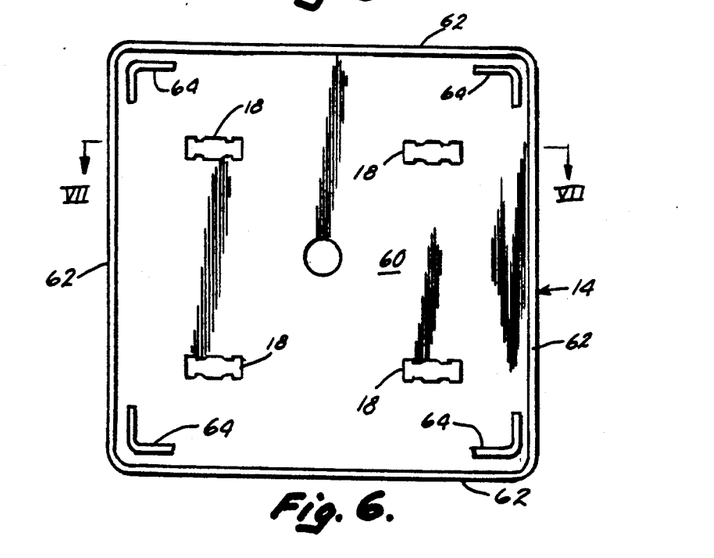
FIG. 6 is a bottom plan view of the rack for the sterilizer assembly.
Figure 7:
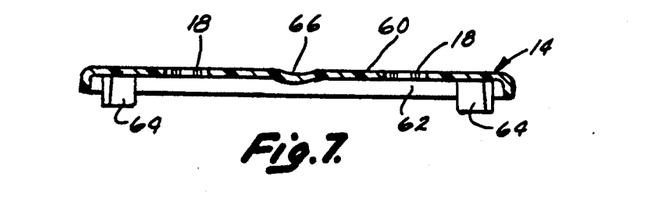
FIG. 7 is a sectional side elevation of the rack taken along plane VII—VII of FIG. 6.
Figure 8:
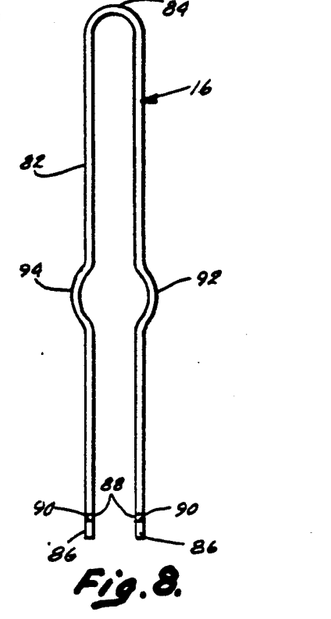
FIG. 8 is a front elevation of one of the supports for the sterilizer assembly.
Figure 9:
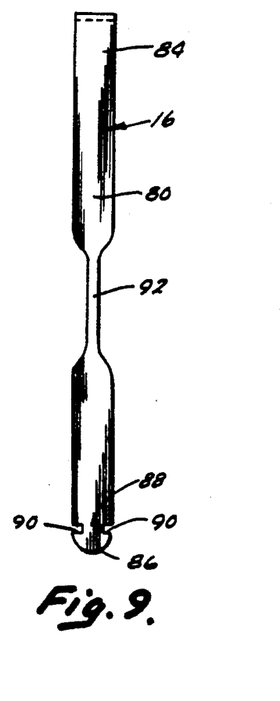
FIG. 9 is a side elevation of the support shown in FIG. 8.
Figure 12:
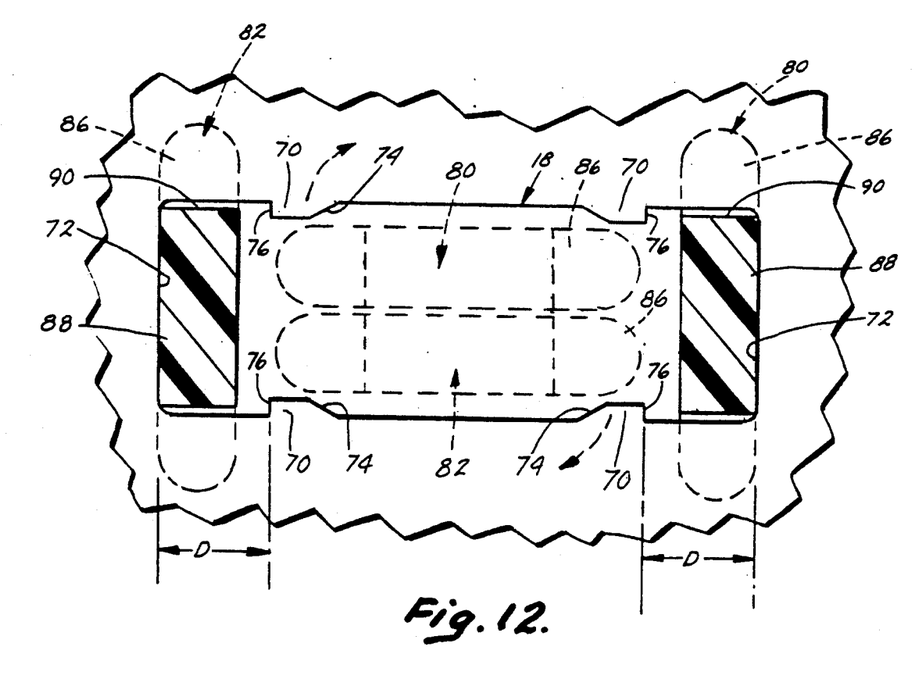
FIG. 12 is a sectional plan view of one of the supports mounted in one aperture in the rack taken along plane XII—XII of FIG. 3.

As shown in FIGS. 1, 2 and 6, apertures or slots 18 are provided on shelf 60 adjacent but spaced inwardly from the corners of rack 14. Apertures 18 are adapted to provide passageways for conducting steam formed when water contained within the assembly is heated by means of a microwave oven as explained hereinafter. As is best seen in FIG. 12, each of the apertures 18 is generally rectangular and includes two pair of inwardly extending stops or shoulders 70. Stops 70 are aligned with one another in each pair and spaced from an end 72 of the aperture by a distance D which is slightly greater than the thickness of legs 80, 82 of supports 16. Each stop includes a cam or ramp surface 74 and a stop surface 76 extending parallel to end surface 72. As explained below, the width between stops 70 is less than the length of connecting portion 88 joining tab 86 to the bottom of support 16. Thus, when received in the end areas between stop surfaces 76 and ends 72, supports 16, and, specifically, connecting portions 88 thereof, are firmly retained unless twisted for removal. Apertures 18 each have a width less than the length of tabs 86 of support 16 but greater than the length of connecting portions 88, a length matched to the overall width of each support 16 (see FIG. 2), and are aligned with and parallel to one another as shown in FIGS. 2 and 6.

With reference to FIGS. 2, 3, 8 and 9, each support 16 is a U-shaped member also preferably molded in one piece and including a pair of generally parallel legs 80, 82 joined by a curved end member 84 at its upper end. At the lower end of each leg 80, 82 are semi-circular mounting tabs 86 spaced from an adjacent portion of each leg by connecting member 88 to form parallel slots 90 having a width slightly greater than the thickness of shelf or platform 60 of rack 14. Generally in the center of each leg 80, 82 intermediate the ends 84, 86 of the legs, are reduced width, outwardly flared, curved, nipple holding portions 92, 94 which are horizontally aligned with one another. Outwardly flared sections 92, 94 are circular in shape and have a common center such that the circular portion of a nipple N is received and frictionally held by the inside surfaces of sections 92, 94 as shown in FIGS. 1-3. As explained below, each support is sufficiently narrow such that it projects into a baby bottle through the mouth of the bottle. End 84 engages the inside surface of the bottle bottom to suspend the bottle with its mouth extending downwardly over aperture 18 to receive steam passing upwardly through the apertures for proper cleaning and sterilization. In addition, the downwardly supported bottle will properly drain should any water condense therewithin during the sterilization process. Alternately, when support 16 is not receiving a baby bottle B as shown in FIGS. 2 and 3, each support may receive one or more of the nipple N, nipple hood H and bottle collar C as illustrated. In such case, nipple hood H is received over and suspended on end 84 with its open end extending downwardly toward aperture 18 in a manner similar to bottle B. Nipple N is inserted and frictionally held in outwardly flared sections 92, 94 such that its open end projects laterally of aperture 18 on an axis extending generally perpendicular to the upright direction of elongation of support 16. Since nipple N is conical or tapered toward its open end, such lateral positioning allows any condensed water within the nipple to drain outwardly during such support. Likewise, collar C is telescoped over support 16 via its central aperture and located concentrically with support 16 by legs 80, 82 while it rests on the top surface of shelf 60.

Figure 5:
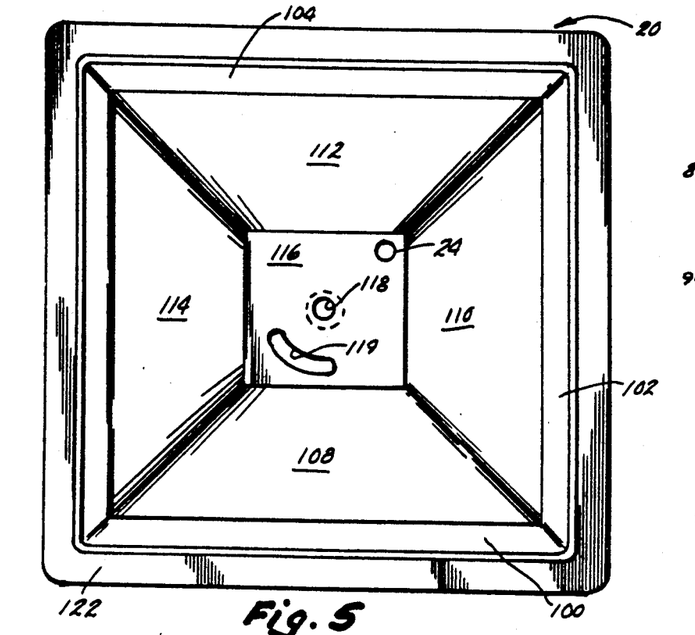
FIG. 5 is a top plan view of the hood or closure for the assembly, the movable vent closure being removed.

As shown in FIGS. 2, 3 and 5, the dome-like closure or hood 20 is also integrally molded in one piece from a heat resistant material useful in microwave ovens. Hood 20 generally has the shape of a truncated pyramid including inclined sidewalls 100, 102, 104 and 106 molded integrally with more steeply inclined, trapezoidal top panels 108, 110, 112, 114 which, in turn, are joined to planar top wall 116 which is perpendicular to the axis of the pyramid. Top wall 116 includes circular vent aperture 24 located near one corner, a circular vent member mounting aperture 118 located at the center of the top wall, and an arcuate slot 119 which receives a portion of vent member 22 to limit rotation of the vent member as described below.

At the lower end of hood 20 the lowermost edges of sidewalls 100, 102, 104, 106 define a co-planar lower edge 120. Spaced slightly above lower edge 120 is a planar support flange 122 which extends continuously around the entire hood as shown in FIG. 5. Hood 20 is supported on base 12 by means of planar flange 122, the undersurface of which contacts and rests on top flange 48 of base 12. The lower perimeter of hood 20 is sized to be slightly smaller than the inside dimension of the interior of base 12. The lower ends of the hood sidewalls 100-106 are telescoped within and fit closely adjacent the inside surfaces of sidewalls 30-36 on base 12 as shown in FIG. 3. As shown in FIG. 3, the outer surfaces of the lower ends of sidewalls 100-106 are relieved to form a slight taper to allow proper fit of the outwardly angled hood sidewalls within the upstanding sidewalls 30-36.

As shown in FIGS. 1-3, 10 and 11, square vent member 22 is rotatably mounted in aperture 118 on top wall 116 on hood 20. Vent member 22 is molded in one piece and includes a planar body 124 having a perimeter 126 corresponding in size to top wall 116, and a T-shaped handle 128 on its top surface. Handle 128 includes a vertical wall 129 and a horizontal top flange 130 which tapers toward its inner end. A mounting projection 132 extends downwardly from the undersurface of body 124 and has a length sufficient to extend entirely through slightly larger support cylinder 121 projecting downwardly below aperture 118 (FIG. 3). Projection 132 includes a pair of spaced, partially cylindrical legs 134 each having an outwardly extending lip or shoulder 136 spaced below body 124 slightly more than the length of cylinder 121 and adapted to engage the underside of that cylinder. Legs 134 flex toward one another when projection 132 passes through cylinder 121 to allow passage of shoulders 136 with a snap-fit action. When cylinder 132 is received in aperture 118, and legs 134 project through cylinder 121, shoulders 136 pass the lower end of cylinder 121 and snap outwardly to retain vent member 22 permanently on top wall 116 but allow rotational movement. Also, cylindrical peg 138 extends downwardly from body 124 beneath the outer end of handle 128 and is received in slot 119 to limit rotation of vent member 22. When vent member 22 is rotated to the left (FIGS. 1, 2 and 11) until peg 138 is stopped by the right end of slot 119, aperture 24 is uncovered to allow escape of residual steam within hood 20 to prevent injury. When rotated to the right, however, until peg 138 is stopped by the left end of slot 119, the imperforate bottom surface of vent body 124 closely covers vent aperture 24 and prevents the escape of steam from the interior of hood 20.

Each part of the assembly 10 is preferably molded in one piece from a heat resistant, microwavable material such as general purpose or clarified polypropylene. General purpose polypropylene is used to mold base 12, rack 14, supports 16 and vent member 22. Hood 20 is formed from clarified polypropylene which is likewise heat resistant and microwavable but is translucent or semi-transparent such that the contents of the sterilizer assembly may be viewed therethrough without opening the assembly. A preferred general purpose polypropylene is that sold under the trademark PRO-FAX from Himont Company of Wilmington, Del. A preferred clarified polypropylene is that sold under the trademark SHELL DX6A01K from Shell Oil Company of Houston, Tex. Such material withstands heat within the range of 225° F. to 250° F. without deforming and is water and steam resistant for durability and long life. Assembly 10 is adapted to be heated in a microwave oven for a typical period of ten minutes at full power. Interior temperatures within the assembly during such heating may reach as high as about 212° F. when steam is generated therein. Such materials can easily withstand those temperature ranges and effectively perform the sterilization or pasteurization function.

The assembly and operation of the sterilizer assembly will now be understood with reference to FIGS. 1-3 and 12. Each of the removable supports 16 is assembled to rack 14 by means of apertures 18. Supports 16 are assembled by grasping and pinching legs 80, 82 toward one another. Sufficient flexibility for such movement is provided by the natural resiliency of the material from which the support is molded and end 84. When the ends of the legs are closely adjacent or touching one another, tabs 86 are inserted through aperture 18 parallel to the length of aperture 18 as shown in phantom in FIG. 12. Legs 80, 82 are then rotated 90° until slots 90 are adjacent cam surfaces 74 on stops 70 as shown by the dotted arrows in FIG. 12. Thereafter, supports 16 are released such that legs 80, 82 return to their normal, parallel positions with slots 90 receiving the edges of shelf 60 adjacent either end 72 of the aperture as shown in FIGS. 1 and 2. Since the distance between stops 70 is slightly less than the length of connecting portions 88, connecting portions 88 must be pressed past stops 70 with the help of cam surfaces 74 which urge the sides of aperture 18 slightly apart when engaged by portions 88. Stop surfaces 76 then resist the removal of legs 80, 82 from the apertures 18 unless and until each leg is slightly twisted or rotated on its lengthwise axis to allow the connecting portion 88 to pass between stops 70. Alternately, legs 80, 82 may also be slightly twisted to insert the connecting portions 88 to past stops 70 when mounting supports 16 in apertures 18. The portions of legs 80, 82 adjacent slots 90 contact the shelf edges surrounding aperture 18 and stably hold support 16 in an upright position on rack 14 as shown in FIGS. 1-3. This procedure is repeated until a support is mounted over each aperture 18 on rack 14.

After assembly of supports 16 to rack 14, a predetermined quantity of water is placed in receptacle 42 on imperforate bottom wall 38. Thereafter, the rack assembly is placed within receptacle 42 such that feet 64 are located adjacent the corners between vertical walls 40b in the receptacle. Feet 64 space shelf 60 above bottom wall 38 and any water in receptacle 42. Infant accessories such as baby bottle B, nipple hood H, nipple N and bottle collar C are then placed on various of the supports 16 as shown in FIGS. 1-3 and as described above. As noted, up to four baby bottles may be supported at any one time with their bottom surfaces suspended on support ends 84 and their mouths immediately adjacent but spaced above apertures 18 as shown in FIG. 3. Alternately, two baby bottles may be supported on two of the supports, while the accompanying accessories for the two bottles are supported on the remaining two supports 16 in the manner shown in FIGS. 1-3. In addition, other items such as pacifiers, nonmetallic baby toys and the like can be placed in the assembly resting on rack 14. Hood 20, with vent 22 snap-fitted thereon, is then placed over the rack 14, supports 16 ad any accessories mounted on supports 16 or rack 14 such that is lower perimeter 120 is telescoped within sidewalls 30-36 and flange 122 supports the hood on top flange 48 of base 12. Flange 48 projects slightly beyond flange 122 to prevent inadvertent lifting of hood 20 by flange 122 in the event the assembly is grasped and lifted by flange 48. Vent 22 is then rotated to the right by means of handle 28 such that aperture 24 is covered to retain any steam buildup within the assembly.

The assembled unit 10 is then placed in a microwave oven by means of handles 50. Typically, the microwave oven is set to provide maximum microwave energy for a period of ten minutes so that the quantity of water in base 12, typically two ounces, will be heated to its boiling point to create steam at a temperature of about 212° F. which is resisted by the polypropylene components of the assembly without degradation or injury to the unit. Such heating and steam generation raises the internal temperature within the microwave oven slightly. Steam generated within base 12 passes around rack 14 and upwardly through apertures 18 into baby bottles B, collars C, nipples N and nipple hoods H for thorough contact and sterilization. Any water condensed on such bottles or parts drains from those parts because they are supported with their openings extending downwardly or laterally downwardly as illustrated. After steam generation and sterilization, typically for a period of ten minutes within a microwave oven, the unit 10 is removed from the oven by means of handles 50 which cool rapidly due to their outward extension and slots 52. When removed from the oven, vent member 22 is rotated by means of handle 128 to uncover aperture 24 and allow release of any entrapped steam within the assembly enclosure. Thereafter, hood 20 may be lifted from base 12 by handle 128 to allow removal of the sterilized baby bottles and parts or other items.

Of course, more or less than four supports 16 could be mounted on rack 14 depending on the site of the rack. It will also be understood that alternative mounting structure could be provided between the ends of supports 16 and rack 14 such as molded sockets in rack 14 which would receive the downwardly projecting ends of legs 16 or other like structures.

It will be understood that each of the parts of the assembly is molded from heat resistant, microwavable material such that the entire assembly is uniquely adapted for use in a microwave oven by avoiding any metallic parts. In addition, each of the parts is easily disassembled to allow thorough washing or cleaning of those parts. In addition, assembly and use of the sterilizing unit is quickly and easily accomplished. In its preferred form, the unit allows sterilization of up to four baby bottles or two bottles including parts thereof simultaneously through the use of the rapid heating action of a microwave oven. Therefore, the present invention allows more efficient, rapid sterilization of all necessary infant accessories at one time. Moreover, through the use of the movable vent member, injuries and burns are avoided by releasing steam from the enclosure prior to opening.

While several forms of the invention have been shown and described, other forms will now be apparent to those skilled in the art. Therefore, it will be understood that the embodiments shown in the drawings and described above are merely for illustrative purposes, and are not intended to limit the scope of the invention which is defined by the claims which follow.

The embodiments of the invention in which an exclusive property or privilege is claimed are defined as follows:

1. A sterilization assembly adapted for sterilizing infant accessories and other items comprising:
   a base including receptacle means for holding a predetermined quantity of water;
   a rack received on said base for supporting items to be sterilized above the water, said rack including an aperture extending therethrough;
   an upstanding support mounted on said rack over and in alignment with said aperture for supporting and locating a baby bottle on said rack,
   said upstanding support including an upper portion spaced above said rack a distance greater than the length of a baby bottle to be suspended thereby, said upper portion engaging the interior of the bottom of the baby bottle and suspending the baby bottle above said aperture with the mouth of the bottle opening downwardly toward and aligned with said aperture but spaced above said aperture and spaced from other supporting structure therebelow to allow steam to circulate both internally and externally of the bottle and to allow any condensed water to drain from the baby bottle;
   said rack being substantially imperforate except for said aperture; said aperture allowing steam to pass through said rack to the baby bottle;
   a dome-like closure supported on said base for enclosing said rack, said upstanding support and any baby bottle thereon during sterilization.

2. The assembly of claim 1 including mounting means for removably mounting said upstanding support on said rack.

3. The assembly of claim 1 wherein said dome-like closure includes an aperture and vent means for opening and closing said aperture to alternately release or retain steam within said assembly as desire.

4. The assembly of claim 3 wherein said vent means include a movable vent member; said dome-like closure including a hollow, upstanding hood having a top wall, said movable vent member including securing means for rotatably mounting said movable vent member on said top wall and handle means for rotating said movable vent member to uncover said aperture.

5. The assembly of claim 1 wherein said base includes upstanding sides defining said base, said upstanding sides including a common top surface; said dome-like closure including flange means for engaging and locating said dome-like closure on said sides upstanding common and said top surface.

6. The assembly of claim 5 wherein said dome-like closure includes a lower perimeter; said flange means including a first downwardly projecting flange which extends around said lower perimeter of said dome-like closure and a second, outwardly extending flange extending at an angle to said first downwardly projecting flange; said first downwardly projecting flange telescoped within and overlapping the upper portion of said upstanding sides; said second outwardly extending flange supporting said dome-like closure on said common top surface.

7. The assembly of claim 1 wherein said dome-like closure includes a vent for releasing steam from within said assembly.

8. A sterilizer assembly adapted for sterilizing infant accessories and other items comprising:
   a base including receptacle means for holding a predetermined quantity of water;
   a rack received on said base for supporting items to be sterilized above the water, said rack including an aperture extending therethrough;
   an upstanding support mounted on said rack over and in alignment with said aperture for supporting and locating a baby bottle on said rack,
   said upstanding supporting including an upper portion for engaging the interior of the bottom of the baby bottle and suspending the baby bottle above said aperture with the mouth of the bottle opening downwardly toward and aligned with said aperture but spaced above said aperture and spaced from other supporting structure therebelow to allow steam to circulate both internally and externally of the bottle, said upstanding support further including holding means for holding a baby bottle nipple above said aperture;
   said rack being substantially imperforate except for said aperture; said aperture allowing steam to pass through said rack to the baby bottle;
   a dome-like closure supported on said base for enclosing said rack, said upstanding support and any baby bottle thereon during sterilization.

9. The assembly of claim 8 including mounting means for removably mounting said upstanding support on said rack.

10. A sterilizer assembly adapted for sterilizing infant accessories and other items comprising;
    a base including receptacle means for holding a predetermined quantity of water;
    a rack received on said base for supporting items to be sterilized above the water, said rack including an aperture extending therethrough;
    an upstanding support mounted on said rack over and in alignment with said aperture for supporting and locating a baby bottle on said rack,
    said upstanding supporting including an upper portion for engaging the interior of the baby bottle and suspending the baby bottle above said aperture with the mouth of the bottle opening downwardly toward and aligned with said aperture but spaced above the aperture to allow steam to circulate both internally and externally of the bottle;
    said upstanding support further including holding means for holding a baby bottle nipple above said aperture, an upright, U-shaped member having a pair of extending legs, and mounting means for removably mounting said upstanding support on said rack including tab means on said legs engagable with said rack adjacent said aperture for releasably attaching said U-shaped member over said aperture;
    said rack being substantially imperforate except for said aperture; said aperture passing steam through said rack to the baby bottle;
    a dome-like closure supported on said base for enclosing said rack, said upstanding support and any baby bottle or nipple thereon during sterilization.

11. The assembly of claim 10 wherein said U-shaped member is sufficiently flexible to allow said legs to be flexed toward one another; said tab means including at least one slot on each leg for receiving said rack adjacent said aperture and retaining portions on each leg adjacent said slot; said aperture having a reduced width for receiving said slot such that said retaining portions hold said legs over said aperture after said legs are flexed toward one another, inserted in said aperture, and expanded outwardly toward the ends of said aperture, and stop means for resisting removal of said legs from said aperture.

12. The assembly of claim 10 wherein said rack includes a plurality of said apertures therethrough, said rack being substantially imperforate except for said plurality of apertures; said assembly including a plurality of said upstanding supports, each of said upstanding supports mounted over one of said apertures with said mounting means, each of said apertures passing steam through said rack to the baby bottle or nipple on said upstanding support mounted over that aperture, whereby multiple baby bottles or nipples may be simultaneously supported and sterilized in said assembly.

13. The assembly of claim 10 wherein said rack includes a generally planar, imperforate shelf except for said aperture therein and a plurality of downwardly extending feet for supporting said generally planar, imperforate shelf in a position spaced above a water retaining surface of said receptacle means.

14. The assembly of claim 13 wherein said receptacle means is a recessed area within said base having a bottom and upstanding sides defining a perimeter; said rack having a shape corresponding to said receptacle means perimeter; said plurality of downwardly extending feet supporting said generally planar, imperforate shelf at a position generally parallel to but spaced above said receptacle means bottom.

15. A sterilizer assembly adapted for sterilizing infant accessories and other items comprising:
  a base including receptacle means for holding a predetermined quantity of water;
  a rack received on said base for supporting items to be sterilized above the water, said rack including an aperture extending therethrough;
  an upstanding support mounted on said rack over and in alignment with said aperture for supporting and locating a baby bottle on said rack,
  said upstanding support including an upper portion for engaging the interior of the baby bottle and suspending the baby bottle above said aperture with the mouth of the bottle opening downwardly toward and aligned with said aperture but spaced above said aperture to allow steam to circulate both internally and externally of the bottle;
  said upstanding support further including holding means for holding a baby bottle nipple above said aperture, said holding means including opposed, outwardly flared sections on said support, said outwardly flared sections defining an opening therebetween sufficient to receive and engage the outside of a nipple such that the nipple is held with its open end extending laterally with respect to said rack aperture;
  said rack being substantially imperforate except for said aperture; said aperture passing steam through said rack to the baby bottle or nipple;
  a dome-like closure supported on said base for enclosing said rack, said upstanding support and any baby bottle or nipple thereon during sterilization.

16. The assembly of claim 15 wherein said upstanding support is elongated in the upright direction; said opposed, outwardly flared sections each having the shape of a partial circumference of a circle, said circle having an axis which is perpendicular to the direction of elongation of said upstanding support and generally parallel to said rack.

17. A sterilizer assembly especially adapted for sterilizing infant accessories and other items comprising:
  a base including receptacle means for holding a predetermined quantity of water;
  a rack received on said base for supporting items to be sterilized above the water;
  a support for supporting and/or locating at least one item such as a baby bottle or nipple hood on said rack in position for contact with steam when generated within said assembly and for drainage of any water condensed thereon;
  said rack including an aperture extending therethrough for passing steam from said receptacle means to the supported item, said rack being imperforate except for said aperture and also including mounting means for removably mounting said support on said rack over and in alignment with said aperture;
  said support including an upper portion spaced above said rack a distance greater than the length of a baby bottle or nipple hood to be supported thereby, said upper portion engaging the interior the interior of the bottom of a baby bottle or the closed end of a nipple hood and suspending the baby bottle or nipple hood above said aperture with the mouth of the bottle or open end of the nipple hood opening downwardly toward and aligned with said aperture but spaced above said aperture and spaced from other supporting structure therebelow to allow steam to circulate both internally and externally of the bottle or nipple hood and to allow any condensed water to drain from the bottle or nipple hood whereby a baby bottle or nipple hood may be suspended on said support in alignment with but spaced above said aperture for contact with the steam passing through said aperture;
  a dome-like closure mounted on said base for enclosing said rack, said support and any items thereon during sterilization.

18. The assembly of claim 17 wherein said dome-like closure includes an aperture for releasing steam from the interior of said assembly and vent means for opening and closing said aperture.

19. The assembly of claim 18 wherein said vent means include a vent member movably mounted over said aperture, said vent member including means for limiting movement of said vent member when opening and closing said aperture.

20. The assembly of claim 19 wherein said dome-like closure is a hollow, upstanding hood having a top wall, said vent member including securing means for rotatably mounting said vent member on said top wall and handle means for rotating said vent member to open and close said aperture.

21. A sterilizer assembly especially adapted for sterilizing infant accessories and other items comprising:
  a base including receptacle means for holding a predetermined quantity of water;
  a rack received on said base for supporting items to be sterilized above the water;
  a support for supporting and/or locating at least one item such as a baby bottle or nipple hood on said rack in position for contact with steam when generated within said assembly and for drainage of any water condensed thereon;
  said rack including an aperture extending therethrough for passing steam from said receptacle means to the supported item, said rack being imperforate except for said aperture and also including mounting means for removably mounting said support on said rack over and in alignment with said aperture;

said support including an upper portion for engaging the interior of the bottom of a baby bottle or the closed end of a nipple hood and suspending the baby bottle or nipple hood above said aperture with the mouth of the bottle or open end of the nipple hood opening downwardly toward and aligned with said aperture but spaced above said aperture and spaced from other supporting structure therebelow to allow steam to circulate both internally and externally of the bottle or nipple hood whereby a baby bottle or nipple hood may be suspended on said support in alignment with but spaced above said aperture for contact with the steam passing through said aperture, said support further including holding means for holding a baby bottle nipple above said aperture; and a dome-like closure mounted on said base for enclosing said rack, said support and any items thereon during sterilization.

22. The assembly of claim 17 wherein said rack includes a plurality of said apertures therethrough and mounting means for removably supporting one of said supports on said rack over and in alignment with each of said apertures; said assembly including a plurality of said supports, each of said supports mounted over one of said apertures by said mounting means, whereby multiple infant accessories such as a baby bottle or nipple hood may be simultaneously supported and sterilized in said assembly.

23. The assembly of claim 17 wherein said rack includes a generally planar, imperforate shelf except for said aperture therein and a plurality of downwardly extending feet for supporting said shelf in a position spaced above a surface of said receptacle means.

24. The assembly of claim 17 wherein said base includes upstanding sides defining said base, said upstanding sides including a common top surface; said dome-like closure including flange means for engaging and locating said dome-like closure on said upstanding sides and said common top surface.

25. The assembly of claim 17 wherein said dome-like closure includes a vent for releasing steam from within said assembly.

26. A sterilizer assembly especially adapted for sterilizing infant accessories and other items comprising:
    a base including receptacle means for holding a predetermined quantity of water;
    a rack received on said base for supporting items to be sterilized above the water;
    a support for supporting and/or locating at least one item such as a baby bottle, nipple or nipple hood on said rack in position for contact with steam when generated within said assembly and for drainage of any water condensed thereon;
    said rack including an aperture extending therethrough for passing steam from said receptacle means to the supported item, said rack being imperforate except for said aperture and also including mounting means for removably mounting said support on said rack over and in alignment with said aperture whereby an item such as a baby bottle, nipple or nipple hood may be mounted on said support in alignment with but spaced above said aperture for contact with the steam passing through said aperture;
    said support including an upright, U-shaped member having a pair of spaced, extended legs and tab means on said legs engagable with said mounting means on said rack adjacent said aperture for releasably attaching said U-shaped member over said aperture; and
    a dome-like closure mounted on said base for enclosing said rack, said support and any items thereon during sterilization.

27. The assembly of claim 26 wherein said U-shaped member is sufficiently flexible to allow said pair of spaced, extending legs to be flexed toward one another; said tab means including at least one slot on each leg for receiving said rack adjacent said aperture and retaining portions on each leg adjacent said slot; said mounting means including portions of said aperture having a reduced width for receiving said slot such that said retaining portions hold said pair of spaced, extending legs over said aperture after said pair of spaced, extending legs are flexed toward one another, inserted in said aperture, and expanded outwardly toward the ends of said aperture, and stop means for resisting removal of said pair of spaced, extending legs from said aperture.

28. The assembly of claim 26 wherein said rack includes a plurality of said apertures therethrough and mounting means for removably supporting one of said supports on said rack over and in alignment with each of said apertures; said assembly including a plurality of said supports, each of said supports mounted over one of said apertures by said mounting means, whereby multiple infant accessories such as a baby bottle, nipple, or nipple hood may be simultaneously supported and sterilized in said assembly.

29. A sterilization assembly adapted for sterilizing infant accessories and other items comprising:
    a base including receptacle means for holding a predetermined quantity of water;
    a rack received on said base for supporting items to be sterilized above the water, said rack including an aperture extending therethrough;
    an upstanding support mounted on said rack over and in alignment with said aperture for supporting and/or locating items such as a baby bottle and nipple on said rack and spaced above and in alignment with said aperture, said upstanding support including an upper portion spaced above said rack a distance greater than the length of a baby bottle to be suspended thereby, said upper portion engaging the interior of the bottom of the baby bottle and suspending the bottle in inverted fashion over and in alignment with said aperture with the mouth of the bottle opening downwardly toward and aligned with but spaced above said aperture and spaced from other supporting structure therebelow to allow steam to circulate internally and externally of the bottle and to allow any condensed water to drain from the bottle, and means for supporting a baby bottle nipple above and in alignment with said aperture such that the open end of the nipple extends laterally with respect to said aperture;
    a dome-like closure supported on said base for enclosing the rack, said upstanding support and any items thereon during sterilization, said dome-like closure including an aperture and vent means for opening and closing said aperture to alternately release or retain steam within said assembly as desired.

30. The assembly of claim 29 wherein said vent means include a movable vent member; said dome-like closure including a hollow, upstanding hood having a top wall, said movable vent member including securing means for rotatably mounting said movable vent member on said top wall and handle means for rotating said movable vent member to uncover said aperture.

31. The assembly of claim 29 wherein said base includes upstanding sides defining said base, said upstanding sides including a common top surface; said dome-like closure including flange means for engaging and locating said dome-like closure on said sides upstanding and said common top surface.

32. The assembly of claim 31 wherein said dome-like closure includes a lower perimeter; said flange means including a first downwardly projecting flange which extends around said lower perimeter of said dome-like closure and a second, outwardly extending flange extending at an angle to said first downwardly projecting flange; said first downwardly projecting flange telescoped within and overlapping the upper portion of said upstanding sides; said second outwardly extending flange supporting said dome-like closure on said common top surface.

33. A sterilizer assembly especially adapted for use with microwave ovens to sterilize infant accessories such as baby bottles and parts thereof, said assembly being formed from heat resistant, microwavable material comprising:
    a base having upstanding sides defining a receptacle for holding a quantity of water;
    a rack for supporting items to be sterilized above the water, said rack including a plurality of apertures extending therethrough at spaced locations;
    a plurality of upstanding supports for supporting and locating items such as baby bottles or nipple hoods on said rack, each of said supports being mounted on said rack over and in alignment with one of said apertures;
    each of said upstanding supports including an upper portion spaced above said rack a distance greater than the length of a baby bottle to be suspended thereby, said upper portion engaging the interior of the bottom of an item such as a bottle or nipple hood and suspending the item above said aperture with an open end of the item opening downwardly toward and aligned with said aperture but spaced above said aperture and spaced from other supporting structure therebelow to allow steam to circulate both internally and externally of the bottle or nipple hood and to allow any condensed water to drain from the bottle or nipple hood;
    said rack being substantially imperforate except for said apertures; said apertures allowing steam to pass through said rack to the bottles or nipple hoods in alignment therewith;
    a hood removably supported on said base and enclosing said rack, said upstanding supports and any items thereon whereby said assembly simultaneously supports multiple types of infant accessories during sterilization.

34. The assembly of claim 33 wherein each upstanding support also includes holding means for holding a baby bottle nipple above said aperture over which that upstanding support is mounted.

35. The assembly of claim 34 including mounting means for removably mounting each of said upstanding supports on said rack.

36. The assembly of claim 33 wherein said hood includes an aperture and vent means for opening and closing said aperture to alternately release or retain steam within said assembly as desired.

37. The assembly of claim 33 wherein said upstanding sides include a common top surface; said hood including flange means for engaging and locating said hood on said sides upstanding and said common top surface.

38. The assembly of claim 37 wherein said hood includes a lower perimeter; said flange means including a first downwardly projecting flange which extends around said lower perimeter of said hood and a second, outwardly extending flange extending at an angle to said first downwardly projecting flange; said first downwardly projecting flange telescoped within and overlapping the upper portion of said upstanding sides; said second outwardly extending flange supporting said hood on said common top surface.

39. The assembly of claim 33 wherein said hood includes a vent for releasing steam from within said assembly.

40. A sterilizer assembly especially adapted for use with microwave ovens to sterilize infant accessories such as baby bottles and parts thereof, said assembly being formed from heat resistant, microwavable material and comprising:
    a base having upstanding sides defining a receptacle for holding a quantity of water;
    a rack for supporting items to be sterilized above the water, said rack including a plurality of apertures extending therethrough at spaced locations;
    a plurality of upstanding supports for supporting and locating items such as baby bottles, nipples or nipple hoods on said rack, each of said supports being mounted on said rack over and in alignment with one of said apertures;
    each of said upstanding supports also including an upper portion for engaging the interior of an item such as a bottle or nipple hood and suspending the item above said aperture with an open end of the item opening downwardly toward and aligned with said aperture but spaced above the aperture to allow steam to circulate both internally and externally of the bottle or nipple hood;
    each upstanding support also including holding means for holding a baby bottle nipple above said aperture over which that upstanding support is mounted;
    said rack being substantially imperforate except for said apertures; said apertures passing steam through said rack to the baby bottles, nipples, or nipple hoods in alignment therewith;
    mounting means for removably mounting each of said upstanding supports on said rack;
    each upstanding support being a U-shaped member having a pair of spaced, extending legs; said mounting means including tab means on said legs engagable with said mounting means on said rack adjacent said aperture for releasably attaching said U-shaped member over said aperture; said support being sufficiently flexible to allow said legs to be flexed toward one another; said tab means including at least one slot on each leg for receiving said rack adjacent said aperture and retaining portions on each leg adjacent said slot; said aperture having a reduced width for receiving said slot such that said retaining portions hold said legs over said aperture after said legs are flexed toward one another, inserted in said aperture, and expanded outwardly toward the ends of said aperture;
    a hood removably supported on said base and enclosing said rack, said upstanding supports and any items thereon whereby said assembly simultaneously supports multiple types of infant accessories during sterilization.

* * * * *

UNITED STATES PATENT AND TRADEMARK OFFICE
CERTIFICATE OF CORRECTION

PATENT NO. : 5,213,776
DATED : May 25, 1993
INVENTOR(S) : Maniero et al.

It is certified that error appears in the above-indentified patent and that said Letters Patent is hereby corrected as shown below:

Column 2, line 42;
  "legs ar" should be --legs are--.

Column 4, line 54;
  "shelf 6" should be --shelf 60--.

Column 7, line 38;
  After "88" delete --to--.

Column 7, line 66;
  "ad any" should be --and any--.

Column 7, line 67;
  "that is" should be --that its--.

Column 8, line 17;
  After "oven" insert --only--.

Column 8, line 36;
  "site" should be --size--.

Column 9, line 1;
  "sterilization" should be --sterilizer--.

Column 9, line 36;
  "desire" should be --desired--.

Column 9, lines 48 & 49;
  "sides upstanding common and said top surface" should be
  --upstanding sides and said common top surface--.

UNITED STATES PATENT AND TRADEMARK OFFICE
CERTIFICATE OF CORRECTION

PATENT NO. : 5,213,776
DATED : May 25, 1993
INVENTOR(S) : Maniero et al.

It is certified that error appears in the above-indentified patent and that said Letters Patent is hereby corrected as shown below:

Column 10, line 37;
  "supporting" should be --support--.

Column 12, line 20 & 21;
  Delete "the interior", second occurence.

Column 14, line 34;
  "sterlilization" should be --sterilizer--.

Column 15, line 9;
  "sides upstanding" should be --upstanding sides--.

Column 16, line 4;
  "sides upstanding" should be --upstanding sides--.

Signed and Sealed this

Nineteenth Day of April, 1994

Attest:

BRUCE LEHMAN

*Attesting Officer*   Commissioner of Patents and Trademarks